United States Patent [19]

Boyle, Jr. et al.

[11] Patent Number: 4,916,207

[45] Date of Patent: Apr. 10, 1990

[54] POLYCARBONATE HOMOPOLYMER-BASED FIBER COMPOSITIONS AND METHOD OF MELT-SPINNING SAME AND DEVICE

[75] Inventors: William J. Boyle, Jr., Denville; Frank Mares, Whippany; Kundan M. Patel, Landing; Reginald T. Tang, Warren, all of N.J.

[73] Assignee: Allied-Signal, Inc., Morris Township, Morris County, N.J.

[21] Appl. No.: 232,408

[22] Filed: Aug. 15, 1988

Related U.S. Application Data

[62] Division of Ser. No. 134,290, Dec. 17, 1987, abandoned.

[51] Int. Cl.$^4$ ............................................. C08G 63/62
[52] U.S. Cl. .................................. 528/ 370; 523/113; 523/114
[58] Field of Search .................. 528/370; 524/113, 114

[56] References Cited

U.S. PATENT DOCUMENTS

| | | | |
|---|---|---|---|
| 3,248,414 | 0/0000 | Stevens | 260/463 |
| 3,301,824 | 1/1967 | Hostettler et al. | 528/354 |
| 3,758,443 | 0/0000 | Konig et al. | 260/75 NP |
| 3,952,016 | 0/0000 | Barillo et al. | 260/340.2 |
| 3,959,185 | 0/0000 | Barrillo et al. | 252/522 |
| 4,052,988 | 0/0000 | Doddi et al. | 128/335.5 |
| 4,070,375 | 0/0000 | Suzuki | 260/340.6 |
| 4,079,038 | 0/0000 | Choi et al. | 260/47 |
| 4,157,437 | 0/0000 | Okuzummi et al. | 528/354 |
| 4,160,853 | 0/0000 | Ammons et al. | 428/425 |
| 4,190,720 | 0/0000 | Shalaby | 528/354 |
| 4,243,775 | 1/1981 | Rosensaft et al. | 525/415 |
| 4,300,565 | 0/0000 | Rosensaft et al. | 128/335.5 |
| 4,423,205 | 0/0000 | Rajan | 528/371 |
| 4,429,080 | 1/1984 | Casey et al. | 525/415 |
| 4,705,820 | 1/1987 | Wang et al. | 524/381 |
| 4,754,017 | 6/1988 | Leitz et al. | 528/371 |
| 4,791,929 | 12/1988 | Jarrett et al. | 128/335.5 |

FOREIGN PATENT DOCUMENTS 1272733  5/1972  United Kingdom .

OTHER PUBLICATIONS

M. S. Roby et al., "Absorbable Sutures Based on Glycolide/Trimethylene Carbonate Copolymers", Cyro Industries, Orange, Conn. p. 216.

L. Vogdanis et al, "Carbon Dioxide as a Monomer", (3a). The Polymerization of . . . Makromol. Chem, Rapid Commun. 7, 543–547 (1986).

H. Keul et al., "Anionic Ring-Opening Polymerization of 2,2-Dimethyltrimethylene Carbonate", Makromol Chem. 187, 2579–2589 (1986).

S. Sarel et al., "The Stereochemistry and Mechanism of Reversible Polymerization of 2,2-Disubstituted . . .", Sep. 5, 1985/Dpt. Pharm. Chem./Hebrew Univ/Hadassah Medical.

B. J. Ludwig et al., "Some Anticonvulsant Agents Derived from 1,3-Propanediols", Dec. 1951/vol. 73, pp. 5779–5781.

S. Sarel et al., "Organic Carbonates, IV. Factors Affecting Formation of . . . ", vol. 24/ Dec. 1959, pp. 1873–1877.

T. Kawaguchi et al., "Release Profiles of 5--Fluorouracil and Its Derivatives from Polycarbonate . . . ", Chem Parm Bultn 20'4, 1517–1520.

T. Kohma et al., "Preparation and Evaluation . . . ", Chem Pharm Bultn 32' 2795–2802.

W. Carothers et al., "Studies on Polymerization and Ring Formation . . . ", vol. 52/Jan. 1930, pp. 314–326.

"New Type of Polymerization of Ethylene Carbonate", Polymer Letters Edition, vol. 14, pp. 161–165 (1976).

K. Soga et al., "Polymerization of Propylene Carbonate", Jrnl of Polymer Science Plymr Chem. Ed., vol. 15, 219–229 (1977).

S. Inouh et al., "Copolymerization of Carbon Dioxide and Epoxide with Organometallic . . . ", Die Makro. . Chemie 139(1969) 210–230 (nr. 3170).

B. Pourdeyhimi, *Textile Progress*, "Vascular Grafts: Textile Structures & Their Performance", vol. 15/No. 3, pp. 1–31.

J. M. Lee et al., "Anisotropic Vascular Viscoelastic Properties of Vascular Graft Materials . . . ", Biomaterials 1986, vol. 7/Dec., pp. 423–431.

*Primary Examiner*—Lewis T. Jacobs
*Attorney, Agent, or Firm*—Richard C. Stewart; Gerhard H. Fuchs

[57] ABSTRACT

Novel polycarbonate homopolymers and implantable bioresorbable medical devices fabricated therefrom.

44 Claims, No Drawings

POLYCARBONATE HOMOPOLYMER-BASED FIBER COMPOSITIONS AND METHOD OF MELT-SPINNING SAME AND DEVICE

This application is a division, of application serial no. 134,290, filed Dec. 17, 1987 now abandoned.

FIELD OF THE INVENTION

This invention relates to fibers and other devices formed in major part from bioresorable homopolymers of polyaliphatic carbonates. These polymers are especially suited for use in devices for implantation into living tissue.

BACKGROUND OF THE INVENTION

Polycarbonates have been known for a number of years. U.S. Pat. No. 3,301,824 (1967) describes the preparation of carbonate homopolymers and random copolymers with cyclic lactones. While the patent generally discloses the polymers as having utility as moldings, coatings, fibers and plasticizers, there is no appreciation whatsoever of biodegradable fibers composed in whole or in part of such polycarbonates.

In addition, there is no appreciation for the usefulness and importance of substituted polyaliphatic carbonates as fiber forming polymeric compositions since in the above patent, it is caprolactone, the dominant co-monomer, which offers the necessary crystalline character needed for fiber formation.

U.S. Pat. Nos. 4,243,775 (1981) and 4,429,080 (1984) disclose the use of aliphatic carbonate-containing polymers in certain medical applications as sutures and medical fasteners. However, this disclosure is clearly limited only to "ABA" and "AB" type block copolymers where only the "B" block contains poly (trimethylene carbonate) or a random copolymer of glycolide with trimethylene carbonate. The A block is necessarily limited to polyglycolide, which is the only component to confer the crystalline character in the polymer (necessary for fiber formation); and the major portion of the polymers is the glycolide.

Accordingly, the art has failed to fully appreciate the potential biological or medical uses of biopolymers based on aliphatic carbonates, especially with respect to their biodegradable or bioresorbable properties, as well as the range of mechanical properties achievable with these materials.

Bioresorbable polymers have been used in the fabrication of devices for implantation in living tissue for several decades. Medical application of such polymers include absorbable sutures, haemostatic aids and, recently, intraosseous implants and slow-released drug delivery systems, to name but a few.

Use of such polymers has been extended to tissue regeneration devices such as nerve channels, vascular grafts, sperm duct channels, fallopian tube ducts or channels and the like. To be effective, these devices must be made from materials that meet a wide range of biological, physical, and chemical prerequisites. The material must be bioresorbable at least in part, nontoxic, noncarcinogenic, nonantigenic, and must demonstrate favorable mechanical properties such as flexibility, suturability in some cases, and amenability to custom fabrication. The biopolymers of the present invention have all of these attributes.

SUMMARY OF THE INVENTION

The present invention provides fiber-forming homopolymers comprising recurring units of the following General Structures I and II:

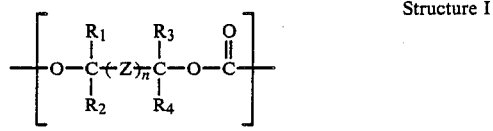

Structure I

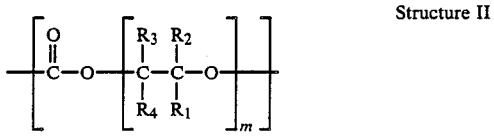

Structure II wherein

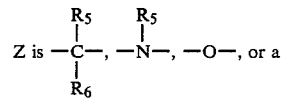

Z is $-\underset{R_6}{\overset{R_5}{\underset{|}{\overset{|}{C}}}}-$, $-\overset{R_5}{\underset{|}{N}}-$, $-O-$, or a combination thereof, where Z is selected such that there are no adjacent heteroatoms;

n and m are the same or different at each occurrence and are integers from about 1 to 8;

$R_1$, $R_2$, $R_3$, and $R_4$ are the same or different at each occurrence and are hydrogen, aryloxyalkyl, alkoxyaryl, aryloxyaryl, arylalkyl, alkylarylalkyl, arylalkylaryl, alkylaryl, arylcarbonylalkyl, alkyl, aryl, alkylcarbonylalkyl, cycloalkyl, arylcarbonylaryl, alkylcarbonylaryl, alkoxyalkyl, or aryl or alkyl substituted with one or more biologically compatible substituents such as alkyl, aryl, alkoxy, aryloxy, dialkylamino, diarylamino, alkylarylamino substituents; and $R_5$ and $R^6$ are the same or different and are $R_1$, $R_2$, $R_3$ $R_4$, dialkylamino, diarylamino, alkylarylamino, alkoxy, aryloxy, alkanoyl, or arylcarbonyl; or any two $R_1$ to $R_6$ together can form an alkylene chain completing a 3, 4, 5, 6, 7, 8 or 9 membered alicyclic fused, spiro, bicyclic and/or tricyclic ring system, which system may optionally include one or more non-adjacent carbonyl, oxa, alkylaza or arylaza groups;

with the proviso that at least one of $R_1$ to $R_6$ is other than hydrogen.

Another aspect of this invention relates to implantable medical devices and fibers formed from the novel homopolymers of this invention, and to prosthetic devices, i.e., sutures, vascular grafts, nerve growth channels, tendon and ligament replacements, and the like, fabricated totally or in part from said fibers.

The present invention is based on the discovery that certain aliphatic carbonates can form highly crystalline homopolymers. The novel homopolymers provided by this invention have relatively high modulus and tensile strength, and can be readily processed to fibers of various deniers, depending on the applications desired. These homopolymers also exhibit controllable biodegradation rates, blood compatability, and biocompatability with living tissue. These homopolymers also induce minimal inflammatory tissue reaction, as biodegradation of the carbonate polymer by hydrolytic depolymerization results in degradation substances having physiologically neutral pH. These particular qualities render fibers made from the homopolymers suitable for medical applications such as vascular grafts, wound and skin covers, sutures, hemostatic aids, materials for tendon or ligament repair, bone or dental repair, and the like.

DETAILED DESCRIPTION OF THE INVENTION

The polymers of the invention comprise the recurring unit of General Structures I and II:

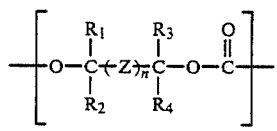

Structure I

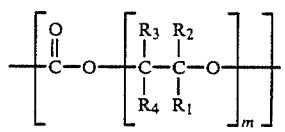

Structure II wherein

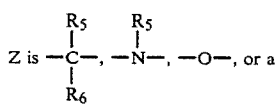

combination thereof, where Z is selected such that there are no adjacent heteroatoms;

n and m are the same or different and are integers from about 1 to 8;

$R_1$, $R_2$, $R_3$, and $R_4$ are the same or different at each occurrence and are hydrogen, aryloxyalkyl, alkoxyaryl, aryloxyaryl, arylalkyl, alkylarylalkyl, arylalkylaryl, alkylaryl, arylcarbonylalkyl, alkyl, aryl, alkylcarbonylalkyl, cycloalkyl, arylcarbonylaryl, alkylcarbonylaryl, alkoxyalkyl, or phenyl or alkyl substituted with one or more biologically compatible substituents such as alkyl, aryl, alkoxy, aryloxy, dialkylamino, diarylamino, alkylarylamino substituents; and $R_5$ and $R_6$ are the same or different and are $R_1$, $R_2$, $R_3$ and $R_4$, dialkylamino, diarylamino, alkylarylamino, alkoxy, aryloxy, alkanoyl, or arylcarbonyl; or any two of $R_1$ to $R_6$ together can form an alkylene chain completing a 3, 4, 5, 6, 7, 8 or 9 membered alicyclic, fused, spiro, bicyclic and/or tricyclic ring system, which system may optionally include one or more nonadjacent carbonyl, oxa, alkylaza or arylaza groups;

with the proviso that at least one of $R_1$ to $R_6$ is other than hydrogen.

Illustrative of useful $R_1$, $R_2$, $R_3$, and $R_4$ groups are hydrogen; alkyl such as methyl, ethyl, propyl, butyl, pentyl, octyl, nonyl, tert-butyl, neopentyl, isopropyl, sec-butyl, dodecyl and the like; cycloalkyl such as cyclohexyl, cyclopentyl, cyclooctyl, cycloheptyl and the like; alkoxyalkyl such as methoxymethyl, ethoxymethyl, butoxymethyl, propoxyethyl, pentoxybutyl and the like; aryloxyalkyl and aryloxyaryl such as phenoxyphenyl, phenoxymethyl and the like; and various alkyl and aryl groups substituted with biocompatible substituents such as 4-dimethylaminobutyl, and the like;

Illustrative of other $R_1$ to $R_4$ groups where two of them form divalent aliphatic chains to form monocyclic, fused, spiro, bicyclic and/or tricyclic ring systems, which chains may optionally include one or more oxa, arylaza, alkylaza or carbonyl groups, such as, —(CH$_2$)$_2$—, —CH$_2$C(O)CH$_2$—, —(CH$_2$)$_3$—, —CH$_2$—CH(CH$_3$)—, —(CH$_2$)$_4$—, —(CH$_2$)$_5$—, —CH$_2$OCH$_2$—, —(CH$_2$)$_2$—N(CH)$_3$CH$_2$—, —CH$_2$C(O)CH$_2$—, —(CH$_2$)$_2$—N(CH$_3$)—(CH$_2$)$_2$—, —CH(CH$_2$CH$_2$)$_2$CH—, —CH(CH$_2$CH$_2$CH$_2$)$_2$CH—, —CH(CH$_2$)(CH$_2$CH$_2$)CH—, —CH(CH$_2$)(CH$_2$CH$_2$CH$_2$)CH—, —CH(C(CH$_3$)$_2$)(CH$_2$CH$_2$)CH—, and the like.

Illustrative of useful $R_5$ and $R_6$ groups are the above-listed representative $R_1$ to $R_4$ groups, including —OCH$_2$C(O)CH$_2$—, —(CH$_2$)$_2$—NCH$_3$—, —OCH$_2$C(O)CH$_2$—, —O—(CH$_2$)$_2$—O—, alkoxy such as propoxy, butoxy, methoxy, isopropoxy, pentoxy, nonyloxy, ethoxy, octyloxy, and the like; dialkylamino such as dimethylamino, methylethylamino, diethylamino, dibutylamino, and the like; alkanoyl such as propanoyl, acetyl, hexanoyl, and the like; arylcarbonyl such as phenylcarbonyl, p-methylphenylcarbonyl, and the like; and diarylamino and arylalkylamino such as diphenylamino, methylphenylamino, ethylphenylamino and the like.

Preferred for use in the practice of this invention are homopolymers having recurring units of General Structure I wherein:

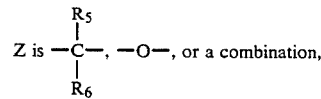

thereof, where Z is selected such that there are no adjacent heteroatoms;

n is 1, 2 or 3; and $R_1$ to $R_6$ are as defined above, preferably where aliphatic moieties included in $R_1$ to $R_6$ include up to about 10 carbon atoms and the aryl moieties include up to about 16 carbon atoms.

Illustrative of these preferred homopolymers are those having recurring units of the General Structure I wherein n is 1 and Z is of the formulas:

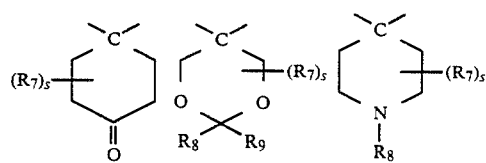

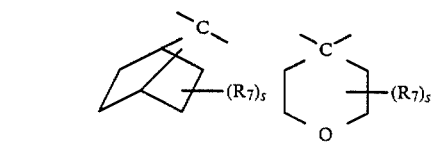

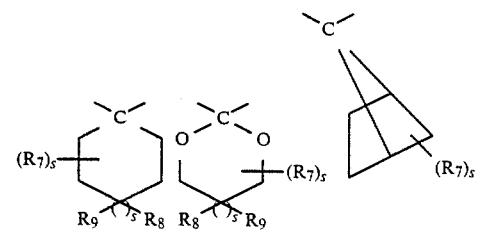

where —C— denotes the central carbon atom of Z, when Z is —C($R_5$) ($R_6$)—; $R_7$ is the same or different at each occurrence and is aryl, alkyl or an alkylene chain completing a 3 to 16 membered ring structure, including fused, spiro, bicyclic and/or tricyclic structures, and the like; $R_8$ and $R_9$ are the same or different at each occurrence and are $R_7$ or hydrogen, s is the same or different at each occurrence and is 0 to about 3, and the open valencies are substituted with hydrogen atoms.

Also illustrative of these preferred homopolymers are those comprising recurring units of the formulas:

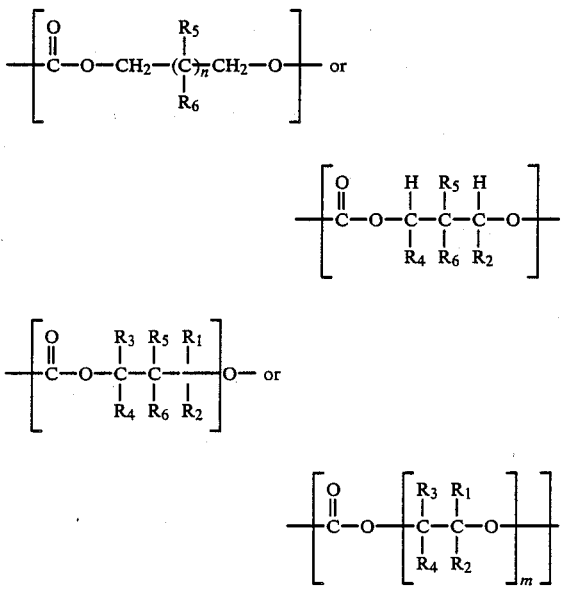

wherein:

n and m are the same or different and are 1, 2, or 3;

$R_1$, $R_2$, $R_3$, and $R_4$ are the same or different at each occurrence and are hydrogen, alkyl such as methyl, ethyl, n-propyl, isopropyl, n-butyl, sec-butyl, t-butyl, neopentyl, and the like; phenyl; phenylalkyl; such as benzyl, phenetyl, and the like; phenyl substituted with one or more alkyl or alkoxy group such as tolyl, xylyl, p-methoxyphenyl, m-ethoxyphenyl, 3-methoxy-4-methylphenyl, p-propoxyphenyl, and the like; and alkoxyalkyl such as methoxymethyl, ethoxymethyl and the like; and $R_5$ and $R^6$ are the same or different and are $R_1$ to $R_4$, alkoxy, alkanoyl, arylcarbonyl, dialkylamino; or any two of $R_1$ to $R_6$ together may form alkylene chain completing 4, 5, 6, 7, 8 or 9 membered spiro, bicyclic or tricyclic ring structures which structure may optionally include one or more non-adjacent divalent carbonyl, oxa, alkylaza or arylaza groups; With the proviso that at least one of $R_1$ to $R_6$ is other than hydrogen; and Particularly preferred for use in the practice of this invention are homopolymers having recurring units of the formula:

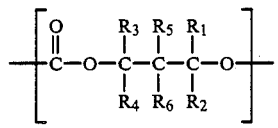

wherein:

$R_1$ to $R_4$ are the same or different and are alkyl, hydrogen, alkoxyalkyl, phenylalkyl, alkoxyphenyl, or alkylphenyl, wherein the aliphatic moieties include from 1 to about 9 carbon atoms; and $R_5$ and $R_6$ are the same or different at each occurrence and are selected from the group consisting of $R_1$ to $R_4$ substituents, aryloxy, and alkoxy, or $R_5$ and $R_6$ together may form an aliphatic chain completing a 3 to 10 membered spiro, bicyclic, or tricyclic structure which may include one or two non-adjacent oxa, alkylaza or arylaza groups, with the proviso that at least one of $R_1$ to $R_6$ is other than hydrogen.

In the most preferred embodiments of this invention, the homopolymer recurring monomeric units of Structure III:

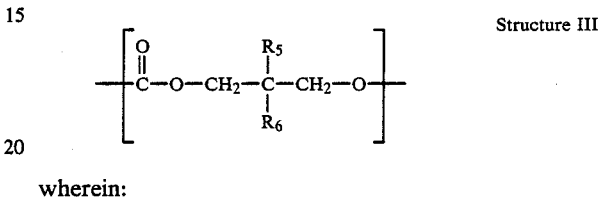

Structure III wherein:

$R_5$ and $R_6$ are the same or different are are hydrogen, alkyl, phenylalkyl, phenyl substituted with one or more alkyl or alkoxy groups or $R_5$ and $R_6$ together make a divalent chain forming a 3 to 10 membered monocyclic, spiro, bicyclic, and/or tricyclic ring structure which may include one or two non-adjacent carbonyl, oxa, alkylaza or arylaza groups, with the proviso that at least one of $R_5$ and $R_6$ is other than hydrogen.

It is more preferred that the homopolymers have recurring monomeric units of Structure III, particularly when $R_5$ and $R_6$ are the same or different and are alkyl, phenyl, alkylphenyl, phenylalkyl, or a divalent chain forming a 3 to 10 membered, preferably 5 to 7 spiro and/or bicyclic ring structure which may optionally include one or two non-adjacent oxa, or carbonyl, groups. It is particularly preferred that R5 and $R_6$ are the same or different and are phenylalkyl, phenyl or alkylphenyl where the aliphatic moieties are from 1 to about 7 carbon atoms such as tolyl, benzyl or phenyl, or lower alkyl of from 1 to about 7 carbon atoms such as methyl, ethyl, propyl, isopropyl, n-butyl, tertiary butyl, pentyl, neopentyl, hexyl, and secondary butyl.

In the most preferred embodiments having recurring units of the Structure III, $R_5$ and $R_6$ are the same or different, and are lower alkyl having from about 1 to about 4 carbon atoms, and do not differ from each other by more than about 3 carbon atoms, and preferably by not more than about 2 carbon atoms. It is particularly preferred that $R_5$ and $R_6$ be the same and be alkyl of about 1 to 2 carbon atoms, and most preferred that $R_5$ and $R_6$ are methyl or ethyl.

The most preferred structures of this invention are those based on General Structure III wherein $R_5$ and $R_6$ are the same and are selected from the group consisting of: $CH_3-$, $CH_3CH_2-$, $(CH_3)_3CH-$, $(CH_3)_3C-$, $(CH_3)_3CCH_2-$, $C_6H_5-$, tolyl, xylyl; or $R_5$ and $R_6$ together form a divalent chain and are: $-(CH_2)_2-$, $-(CH_2)_3-$, $-(CH_2)_4-$, $-(CH_2)_5-$, $-CH_2OCH_2CH_2OCH_2-$, $-OCH_2CH_2O-$, $-OCH_2CH_2CH_2O-$; or $R_5$ and $R_6$ together form a divalent chain such that $R_5R_6C$ is bicyclo[2.2.1]heptan-7-yl, bicyclo [3.2.1]octan-8-yl, and spiro[3.4]octan-3-yl.

The polymers of this invention are useful in the fabrication of totally or partially bioresorbable medical devices. These devices take many forms depending on intended use. Illustrative of useful devices which may be fabricated from the polymers of this invention are orthopedic devices such as pins, plates, clamps, screws and plates; vascular implants or supports such as arterial grafts; clips; staples; nerve channels or supports; and the like. Illustrative of still other devices which can be fabricated totally or in part from the polymers of this invention are devices for tendon and ligament replacement, breast prostheses, dental packs, sponges, hernia patches, burn dressings, absorbant swabs, and the like. Devices fabricated from the polymers of this invention may be totally bioresorbable or may be fabricated in part from biodurable materials which are relatively resistant to biodegradation. Illustrative of useful biodurable materials are silicone, silicone rubber, polyethylene, polyethylene terephthalate, polyfluoroethylene, polyphosphazene, polyurethane, segmented polyurethane, and the like. Also useful are biodurable metallic substances such as titanium stainless steel, and alloys such as chrominium-cobalt-molybelenum alloys, titanium-aluminum-vanadium alloys, and the like.

The polymers of the invention are particularly suited to be spun into fibers by any suitable fiber-forming technique, which fibers can then be fabricated in useful medical devices using conventional techniques. For example, fibers of the present invention may be formed by conventional processes such as spinning techniques, including melt, solution, dry, gel, and the like. These types of processes are detailed in such sources as Fundamentals of Fiber Formations by Androzej Ziabuke, Wiley and Sons, 1976.

The present inventors attribute the fiber-forming characteristics of the polymers of the invention to the molecular weight range of the polymer, as well as its crystallinity. They have discovered that the polymerization process is critical in attaining these desired fiber-forming characteristics. For example, the polymerization of monomeric cyclic carbonate units may be effected by any acceptable process, such as ring-opening polymerization by melt or solution polymerization, and the like. However, a metal salt polymerization catalyst should be utilized. Of these may be mentioned salts as alcoholates, halides, or carboxylates of tin and the like. Illustrative of these are stannous octoate, stannous acetate, stannous chloride, stannous butoxide, stannous ethoxide, and the like. However, stannous chloride and stannous octoate are particularly preferred.

In addition, for certain applications, end-capping of these biopolymers may be desirable. End-capping by, e.g., aceylating, alkylating, silylating agents and the like are definitely within the scope of this invention. Also included are chain extending and grafting of various other units, monomeric, oligomeric or polymeric, or otherwise. These are techniques well known in the art of polymer science. Preferred parts per million (ppm) range from about 5 ppm to 800 ppm, with about 25 ppm to 500 ppm more preferred, and about 75 ppm to 200 ppm most preferred.

Reaction time varies widely according to scale and molecular weight ranges desired. However, typical times range from about 0.5 hours to about 168 hours, with about 1 hour to about 6 hours being preferred.

Reaction temperatures may vary widely. In general, the reaction temperature will depend on the method employed to polymerize the polymer, i.e., a solution of melt polymerization. For melt or bulk polymerization, the reaction temperatures are equal to greater than about the melting temperature of the monomers. In general, for melt polymerization, preferred temperatures range from about 100° C. to about 300° C., with about 150° C. to about 200° C. particularly preferred.

The molecular weight of the polymer may vary widely, depending on the use. In general, the molecular weight of the polymer is sufficiently high to allow its use in the fabrication of medical devices. In the preferred embodiments of this invention where the polymers are used in the formation of fibers, the polymers are of "fiber-forming molecular weight." As used herein, a "fiber-forming molecular weight" is a molecular weight which is such that the polymers can be spun into a fiber. Such molecular weights and their selections are well known in the art.

Useful average molecular weight ranges of the polymers for use in any particular situation will vary widely depending on the ultimate fiber properties and characteristics it is desired to obtain, such as modulus, tensile strength, bioresorption and biodegradation rates, and the like. In general, polymer molecular weights useful for forming fibers of the invention are equal to or greater than about 10,000. Preferred average molecular weight ranges are from about 10,000 to about 5,000,000, with a range of from about 20,000 to about 1,000,000 being particularly preferred, and a range of from about 30,000 to about 500,000 being most preferred.

The molecular weight distribution of the polymer may vary widely. To improve the physical properties of the polymer, it is preferred to maintain the molecular weight distribution of the polymer within a preferred range using conventional techniques as for example fractionation. The molecular weight distribution is commonly calculated as a dispersity number, which is the weight average molecular weight divided by the number average molecular weight (number of polymer units of a particularly molecular weight). The dispersity number of polymers for use in implantation devices of this invention is preferably equal to or less than about 10.0; more preferably is equal to or less than about 3.0; and most preferably is from about 1.0 to about 1.9.

Other polymeric components such as fillers and binders may be combined with the polymers prior to and during the formation of fibers or devices, or subsequent to their formation. These include, but are not limited to polymers and copolymers selected from the group consisting of polyesters such as poly(butyleneterephthalate) and poly(ethyleneterephthalate); polyvinylalcohol; polyvinylacetate and partially hydrolyzed forms thereof; hydrogel type polymers such as poly hydroxyethylmethacrylate, poly hydroxypropylmethacrylate, and the like; polysulfones such as polyphenylenesulfone; carbon; silicon carbide; halopolymers such as poly(tetrafluoroethylene) ethylene/tetrafluoroethylene copolymer; polydioxanone; polyglycolide-co-trimethylene carbonates; polylactides; poly-d-lactide; polylactide-co-caprolactone; poly-d,l-lactide; polycaprolactones; polyhydroxybutyrates; poly hydroxyvalerates; polyhydroxybutyrate-co-hydroxyvalerates; polyglycolide; polyurethanes; segmented polyurethanes; polyetherurethanes; polyurethane ureas; silicone rubber; and substances such as fibrin and its powder; natural or processed collagen; mono, di, tri, and polysaccharides; polyethylenes; polyamides; polypropylene, polycarbonates; poly(vinyl fluoride); poly(vinylidene fluoride); poly(vinyl butyral); cellulose such as, carboxylmethyl cellulose, cellulose acetate, ethylcellulose, and the like; ethylene-vinylacetate copolymers and hydrolyzed and partially hydrolyzed forms thereof; polyacrylonitrile;

poly(vinylmethylether); and their derivative, copolymers and the like.

It is also within the contemplation of the invention that fibers be formed by co-extrusion of different components, organic or inorganic in nature and polymeric or otherwise, together with the polycarbonate fiber materials of the invention. These include, but are not limited to, sheath-core and multiple component, multi-layered types of fiber as well as hollow fibers and hollow fibers, or tubings of concentric multiple layered configuration.

Other components besides polymeric components may be combined with the polymers during or before they are formed into the fibers of the invention, or added to, coated onto and the like, after their formation. These components include substances that will enhance certain of the desired properties of fibers made from the polymers. Among the contemplated classes of such substances are plasticizers, lubricants, antioxidants, stabilizers of all kinds such as stabilizers for UV, radiation, heat, moisture, and the like, as well as drugs for treatment of certain disorders or diseases. Materials such as calcium phosphate salts, ceramics, bioresorbable or otherwise, such as calcium hydroxyapatite, Bioglass, and calcium triphosphate may also be combined with the polymer. Components such as certain barium salts to render the fibers and devices formed from them radio-opaque are also within the contemplation of the invention. Certain of these fillers, binders, additives and components can be removed or leached from such fibers, at some stage, so that a porous or semi-porous system can be obtained. In addition, gas foaming during the extrusion of the fibers either by gaseous, e.g., $N_2$, He, Ar, Ne, $O_2$, and the like, and/or their combinations, or chemical foaming agents, can be utilized to achieve a porous or somewhat porous fiber structure.

Shapes of the fibers can vary. Shapes such as round, oval, square, rectangular, star shaped, shaped generally characterized as multilobal such as trilobal and hexalobal, semispherical, semitorroidal, semi-arched, semi-bowed, semi-oblong, and their combinations and the like are included. Cross-sectional dimensions as well as surface properties such as roughness, smoothness, striations on the long axis as well as circumferential ridges and valleys and the like are important with respect to intended use. Hollow fibers are also included. For example, smooth fibers may be important for applications such as vascular graft, woven or knitted from such smooth fibers; striated fibers may be important as ligament or tendon prosthesis to encourage certain alignment of cells; hollow fibers and multilobal fibers may be especially important for their use in situations where absorbancy is needed. In addition, applications from sub-denier size fibers to sizes such as ribbons and tapes can be envisaged for those skilled in the art.

The fibers of the present invention are useful in the formation of a variety of devices. The fibers and/or yarns braided or twisted from one or more types of fibers may be woven, braided and/or knitted into fabrics having various structural configurations as for example tubes or knitted, woven or felted fibrillar products, such as velours. For example, such fibers and/or yarns may be used in the fabrication of various types of articles having medical applications using conventional techniques. The fibers of this invention are preferably used in the fabrication of implantable medical devices such as vascular implants, and nerve channels; burn and wound covers; facial substitutes; orthopedic substitutes for bone or bone repair; breast prostheses; tendon and ligament replacements; hernia patches; sutures and fasteners, and the like. Other devices not necessary for implantation purposes can also be envisaged, e.g., cell culture substrates, absorbants or swabs, medicated dressings, gauze, fabric, sheet, felt or sponge for hemostasis, dental packs and the like. A good description of the formation of bioresorbable materials in part, or in total as matted surgical dressings may be found in U.S. Pat. No. 3,937,223 to Roth. In particular, hollow fibers or tubings of this invention, may be used for devices where bio- and/or blood-compatibility is most desired, e.g., tubings for transferring blood or other bodily fluids from one place to another.

Particularly useful are woven or knitted fabrics which are formed into tubular prostheses of varying shapes, lengths and diameters, for short or long terms implantation. Illustrative of these tubular prostheses are vascular grafts, nerve guidance channels and the like. The particular configuration of such tubes may vary according to the size and shape of the organ to be repaired, and whether the intended repair is to take place in human surgery or in animal surgery.

The polymers of the invention are particularly suited for use in the formation of vascular repair grafts. Such grafts can be fabricated in conventional configurations as for example hollow tubes, tubular devices formed from fabrics and the like. The polymers of the present invention can induce a limited amount of macrophages infiltration into the area of tissue repair which aids in the absorption of the polymer and other bioresorbable materials, which may be present to aid in the formation of organized tissue such as capillary blood vessels. The polymers of the present invention can induce this biological phenomenom. For vascular graft applications, the internal diameter commonly found useful are in the range from 0.1 mm to 30 mm.

In the preferred embodiments of the invention, especially for, vascular graft applications, the device is pre-treated to provide a more complaint prostheses. Any conventional method can be used. One of the preferred pre-treatment methods is crimping. Illustrative of useful crimping methods is the method described in U.S. Pat. No. 3,337,673. In this method, the spacing and height can be controlled. The crimping of commercially-available Dacron vascular grafts (including both woven and knitted) was about one millimeter up and millimeter down from the mean diameter of the grafts. Crimping as such can be achieved by this method for the bioresorbable grafts.

In the preferred embodiments, the vascular graft is coated with a bioresorbable coating to improve graft patency. Preferably the desired coating is an amorphous polycarbonate, which has some solubility in a solvent which is is a non-solvent for the polymer forming the graft body. In general, the coating is applied to the graft by dissolving the coating polymer in a solvent which is a non-solvent for the graft polymer, and then dipping the graft body into the solution. Illustrative of useful solvents is dimethyl sulfoxide (DMSO), which will dissolve the amorphous polycarbonates which form the coating but not the extruded and more crystalline polymers which form the graft body. The coating solution containing up to about 10% solid can be made with DMSO. For example, a completely clean bioresorbable graft when dipped into a 4.5% solution (six dips, with inversion between each dip) yielded a roughly 25% weight gain. The grafts become slightly stiffer, but the fiber forming the graft body can still be separated down to the monofilaments.

The polymers of the invention are also suited for use in ligament and tendon replacements. Organized tissue formation is encouraged by the use of the polymers of this invention, and which aids in ligament and tendon regeneration.

Similarly, the fibers of the invention are also particularly useful in dental and bone repair. In this application as fibers and fabric formed therefrom may be used in composite structures, with or without such materials as calcium hydroxyapatite, Bioglass, calcium triphosphate, drugs, and the like.

Similarly, fibers of the present invention may also be woven, felted, knitted, braided or the like into nerve guidance channels of many sizes and configurations. U.S. Pat. No. 3,833,002 to Palma discloses various sizes and shapes fabric may be formed into. Lengths of the tubes, internal diameters, and tubular wall thicknesses and wall porosity may vary according to intended use. The length of the tube would ordinarily be commensurate with the size of the nerve gap to be repaired, also allowing extra tubing in which to insert nerve stumps. Particularly useful internal diameters for nerve channels commonly range from about 0.1 mm to 15.0 mm.

Fibers that differ in modulus, although having the same fiber composition, can be obtained by cold draws or similar processes known to those skilled in the art. For those skilled in the art, it should be appreciated that softened fibers are preferred in certain end applications such as wound dressing, swabs, wound or burn covers, as part of vascular protheses, and the like. Fiber of different or the same polymeric compositions and physical and mechanical properties but differing in denier can be obtained and used or fabricated into fabric that is woven, knitted, velveted, veloured, meshed or braided. Staple fibers can be obtained and processed to fabric such as felt, mat and the like. For example, the felted material may be used as, or be part of, skin or wound covers, reinforcements for suturing in surgery, and as aids for hemostasis. Velveted material is particularly suited for use in small caliber blood vessel replacements. Matted fabric may be used, for example, as swabs. Additionally, it should be appreciated that all these forms of fabric and fiber and yarn can be used as slow release drug carriers, not only limited to transdermal, but also used in implantable devices for long or short term procedures.

Hollow fibers, with or without wall porosity, are devices already in tubular form, and can be used as nerve regeneration guidance channels, vascular grafts, fallopian tube duct, sperm duct channels, and the like.

Thus, for those skilled in the art, it can be appreciated that aside from the polymeric composition and molecular weight and distribution of the copolymers of the invention, processing particulars such as those described above can be profitably utilized or adjusted to achieve varying outcomes in biodegradation or bioresorption rates, hardness, toughness, softness, compliancy, adaptability, amenability to custom fabrication during manufacturing and also in the field during the application of the device. This includes combining fibers of the invention with other bioresorbable fibers, fabrics, or devices. For example, any combination with Vicryl, Maxon, Dexon, PDS (polydioxanone), and like, and other type of carbonate based fibers is within the contemplation of the present invention.

However, the present inventors do not wish the applications of the fibers of this invention to be limited to totally biodegradable or bioresorbable devices. Fibers or yarns formed from the polymers of the invention with or without other more biodurable components in the fiber or as part of a device, and/or combinations with other physical objects, are within the contemplation of the invention. These include but are not limited to fabrics and/or coated fabrics in a permanent prosthesis or device, implanted into living organisms or otherwise; fabrics and yarns composed of a mix of fibers or more biodurable fibers and the fibers of this invention; and the like.

The following are more specific examples of certain embodiments of the invention, but are not be construed as limitative thereof.

EXAMPLES

Example 1

Synthesis of 5,5-Dimethyl-1,3-dioxan-2-one (Dimethyltrimethylene Carbonate ("DMTMC")).

A three liter three-necked round bottom flask was fitted with mechanical stirrer, 12 inch Vigreux column with distilling head and a thermometer. In the flask were placed 838 g (8.05 miles) 2,2-dimethyl-1,3-propanediol and 1098 mL (9.07 moles) diethyl carbonate. The mixture was immersed in an oil bath, heating initiated, and the stirrer started. By the time the temperature reached about 90° C., the diol had melted and dissolved in the carbonate. Powdered, dry sodium methoxide (21.6 g, 0.4 moles) was added through the neck used for the thermometer. The bath temperature was raised to 160° C.; ethanol began to distill out.

Over a period of about three hours, approximately 600 g (80% of theoretical) of distillate was collected; this is mainly ethanol with some diethyl carbonate. The reaction mixture gradually became very thick. Dry xylene (200 mL) was added through the top of the distilling column and the bath temperature was raised to 170°–180° C. Additional distillate was collected and the pot temperature gradually climbed to about 150° C.; when the distillation rate had slowed to only a few drops a minute, vacuum was cautiously applied to the system and gradually increased as the xylene and excess diethyl carbonate distilled out.

When the vacuum reached about 2–5 mm Hg, the product carbonate began to distill at about 125°–135° C. At this point, the vacuum was released with dry nitrogen and the oil bath lowered. The Vigreux column and distilling head were removed and replaced with a short path distillation head. Additional powered sodium methoxide (5.4 g, 0.1 moles) was added quickly through the thermometer port.

Vacuum was applied to the system and adjusted to about 3–5 mm Hg. Heating was resumed and the product began to distill out. The bath temperature was raised to 210°–220° C. gradually in order to maintain the depolymerization rate of the oligomers to generate the product monomer. Care had to be taken not to rush the distillation, so that depolymerization of the dimer and oligomers could occur; otherwise, the dimer would have begun to distill over. Eventually, the pot residue, became a gummy lump coated with powder and distillation ceased. Total yield of distillate was 852 g (81% of theory).

The product was a slightly sticky solid due to contamination with small amounts of impurities, such as xylene, diethyl carbonate, the starting diol and the cyclic dimer. It was recrystallized as follows. The total crude DMTMC (852 g) was dissolved in 430 mL tetrahydrofuran and 4.3 liters of anhydrous diethyl ether was added cautiously. The liquors were allowed to stand at room temperature for about one-half hour, then placed in a refrigerator at 4° C. overnight. The crystals were collected by filtration, washed with cold ether (1.2 liters), with hexane (1.2 liters), and then by pulling air through the filter cake for about one hour. Final drying was in a vacuum oven at 35°–40° C. (0.1 mm Hg.). Total recovery of purified DMTMC was 730 g (70% overall yeild).

Example 2

Polymerization of DMTMC.

A freshly purified and dried sample of dimethyl-trimethylene carbonate (12.1 g, 90 mmol) was loaded into a 15 mL polymerization tube. The tube was connected to a vacuum line via a rubber tubing and a stopcook, evacuated, and the DMTMC melted carefully with a heatgun. The tube was cooled in the ice water, evacuated again, remelted, and cooled in ice. Vacuum was released with argon, the stopcook removed, and a solution of stannous octoate in toluene (100) L of $3.0 \times 10^{-2}$M solution, 0.003 mmol) was added. The stopcook was reattached, the tube evacuated for several minutes to remove the toluene, then sealed with a torch. The contents of the tube were melted and thoroughly mixed, then the tube was immersed in an oil bath at 160° C. for 18 hours, cooled and broken. The polymer was dissolved in 250 mL chloroform, precipitated into 2 L of 2-propanol, washed with additional 2-propanol and dried in a vacuum oven at 50° C. The resulting powdery polymer (10 g, 83%) had a reduced viscosity of 3.0 dL/g (0.1% solution in dioxane).

Example 3

Fiber Spinning

The polymer of Example 1 was melt spun at 160° C. into a 70 denier filament. The material appears to crystallize very rapidly. Sections of yarn were hand drawn to approximately 30 denier and tested. Satisfactory fiber properties for fabric and hollow fiber applications were achieved. Fiber properties are: Denier (55); Tensile Modulus (59 grams/denier); Tensile Strength (3 grams/denier); Ultimate Elongation (26%).

Example 4

Tendon and Ligament Replacement Devices

Tendon and ligament replacement devices can be fabricated from homopolymers using the following techniques.

A. Unaxial towed fiber device

A bundle of well aligned fibers roughly with cross-sectional dimensions of 5-6 mm by 0.4-0.5 mm and with a length of 45 cm are fastened onto two surgical needles. The device is cleaned with 0.05% Trinton X-100 in 50% ethanol-water, then rinsed six times with water, and finally rinsed with absolute alcohol. The operation is performed inside a class 100 laminar flow hood from the cleaning of the device up to and including packaging of the device in sterilization bags. Standard cold cycle ethylene oxide is used to sterilize these devices.

The device of this size is useful for tendon or ligament replacements in small animals, e.g., the Achilles tendon in rabbits.

B. Braided and crocheted fabric devices

Six yarns of twisted fibers are braided together to form a strand of fabric 45 mm in length and with cross-sectional dimensions of 1 mm by 6 mm. Similarly, yarns are crocheted into devices of various cross-sectional diameter and length, depending on the end application. These fabrics are cleaned as discussed above and are to be used as replacement devices for ligaments and tendons in small animals.

What is claimed is:

1. An implantable medical device fabricated totally or in part from a homopolymer having recurring monomer units of the following General Structure I or II:

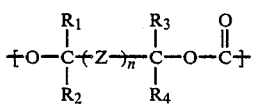

Structure I

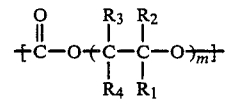

Structure II wherein:

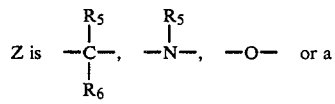

combination thereof, where Z is selected such that there are no adjacent heteroatoms;

n and m are the same or different and are integers from about 1 to 8;

$R_1$, $R_2$, $R_3$ and $R_4$ are the same or different at each occurrence and are hydrogen, aryloxylalkyl, alkoxyaryl, aryloxyaryl, arylalkyl, alkylarylalkyl, arylalkylaryl, alkylaryl, arylcarbonylalkyl, alkyl, aryl, alkylcarbonylalkyl, cycloalkyl, arylcarbonylaryl, alkylcarbonylaryl, alkoxyalkyl, or aryl or alkyl substituted with one or more alkyl, aryl, alkoxy, aryloxy, dialkylamino, diarylamino or alkylarylamino substituents; and $R_5$ and $R_6$ are the same or different and are $R_1$, $R_2$, $R_3$, $R_4$, dialkylamino, diarylamino, alkylarylamino, alkoxy, aryloxy, alkanoyl, or arylcarbonyl, or any two of $R_1$ to $R_6$ together may form an alkylene chain completing a 3, 4, 5, 6, 7, 8 or 9 membered alicyclic fused, spiro, bicyclic, tricylic ring system or a combination thereof, which system may optionally include one or more non-adjacent carbonyl, oxa, alkylaza or arylaza groups;

With the proviso that at least one of $R_1$ to $R_6$ is other than hydrogen.

2. An implantable medical device according to claim 1 which further comprises a biodurable portion.

3. A fiber comprising a homopolymer having recurring monomer units of the following General Structure I or II:

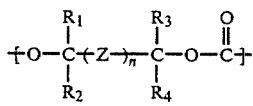   Structure I

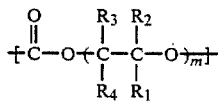   Structure II wherein:

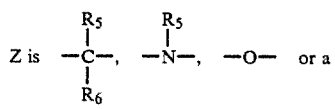

combination thereof, where Z is selected such that there are no adjacent heteroatoms;

n and m are the same or different and are integers from about 1 to 8;

$R_1$, $R_2$, $R_3$ and $R_4$ are the same or different at each occurrence and are hydrogen, aryloxyalkyl, alkoxyaryl, aryloxyaryl, arylalkyl, alkylarylalkyl, arylalkylaryl, alkylaryl, arylcarbonylalkyl, alkyl, aryl, alkylcarbonylalkyl, cycloalkyl, arylcarbonylaryl, alkylcarbonylaryl, alkoxyalkyl, or aryl or alkyl substituted with one or more alkyl, aryl, alkoxy, aryloxy, dialkylamino, diarylamino or alkylarylamino substituents; and $R_5$ and $R_6$ are the same or different and are $R_1$, $R_2$, $R_3$, $R_4$, dialkylamino, diarylamino, alkylarylamino, alkoxy, aryloxy, alkanoyl, or arylcarbonyl, or any two of $R_1$ to $R_6$ together may form an alkylene chain completing a 3, 4, 5, 6, 7, 8 or 9 membered alicyclic fused, spiro, bicyclic, tricylic ring system or a combination thereof, which system may optionally include one or more non-adjacent carbonyl, oxa, alkylaza or arylaza groups;

With the proviso that at least one of $R_1$ to $R_6$ is other than hydrogen.

4. An implantable medical device fabricated totally or in part from the fiber of claim 3.

5. A medical device according to claim 4 which is a fabric woven from fibers of claim 3.

6. A medical device according to claim 4 which is a nerve channel device, tubularly woven from the fiber of claim 26.

7. A medical device according to claim 4 which is a vascular graft device, tubularly woven from the fiber of claim 3.

8. A medical device according to claim 4 which further comprises a biodurable portion.

9. A medical device according to claim 1 wherein $R_1$, $R_2$, $R_3$ and $R_4$ are the same or different and are selected from the group consisting of hydrogen, alkyl, cycloalkyl, alkoxyalkyl, aryloxyalkyl, aryloxyaryl, arylalkyl and aryl and arylalkyl groups substituted with one or more alkyl, alkoxy and alkoxyalkyl groups.

10. A medical device according to claim 9 wherein $R_1$, $R_2$, $R_3$ and $R_4$ are the same or different and are selected from the groups consisting of hydrogen, alkyl, cycloalkyl, alkoxyalkyl, phenylalkyl and phenyl substituted with one or more alkyl or alkoxy groups.

11. A medical device according to claim 10 wherein

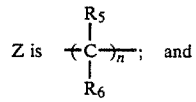

n is 1, 2, or 3.

12. A medical device according to claim 11 wherein $R_1$ to $R_6$ are selected from the group consisting of substituents in which aliphatic moieties include up to about 10 carbon atoms and aryl moieties include up to about 16 carbon atoms.

13. A medical device according to claim 12 wherein n is 1 or 2 and Z is —[C($R_5R_6$)$_n$—].

14. A medical device according to claim 12 wherein said homopolymer comprises a recurring moiety selected from the group consisting of:

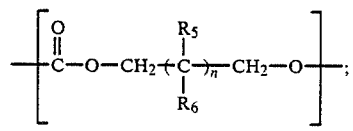

wherein:

$R_5$ and $R_6$ are the same or different and are hydrogen, alkyl, aryl, cycloalkyl, arylalkyl, alkoxyalkyl, aryloxyalkyl, or aryl or arylalkyl substituted with one or more alkyl or alkoxy groups alkoxy, alkanoyl, dialkylamino, or $R_5$ and $R_6$ together may form an alkylene chain completing a 4, 5, 6, 7, 8, 9 or 10 membered spiro, bicylic, tricyclic ring structure or a combination thereof, which structure may optionally include one or more non-adjacent divalent carbonyl, oxa, alkylaza or arylaza groups, with the proviso that at least one of $R_5$ or $R_6$ is other than hydrogen; and n is 1, 2 or 3.

15. A medical device according to claim 1 comprising a recurring unit of the formula:

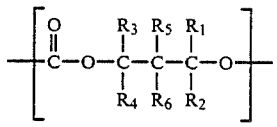

wherein:

$R_1$ to $R_4$ are the same or different and are alkyl, hydrogen, alkoxyalkyl, phenylalkyl or phenyl substituted with one or more alkyl or alkoxy groups, wherein the aliphatic moieties include from about 1 to about 9 carbon atoms; and $R_5$ and $R_6$ are the same or different at each occurrence and are selected from the group consisting of $R_1$ to $R_4$ substituents, aryloxy and alkoxy, or $R_5$ and $R_6$ together form an aliphatic chain completing a 3 to 10 membered ring structure, with the proviso that at least one of $R_5$ or $R_6$ is other than hydrogen.

16. A medical device according to claim 9 wherein;

$R_5$ and $R_5$ are the same or different and are hydrogen, phenyl, phenylalkyl, phenyl substituted with one or more alkyl or alkoxy groups, or alkyl; or $R_5$ and $R_6$ together may form a divalent alkylene chain forming a 3 to 10 membered spiro, bicylic, tricyclic ring structure or a combination thereof, which may optionally include one or more non-adjacent divalent carbonyl or oxa groups, with the proviso that at least one of R₅ and R₆ is other than hydrogen.

17. A medical device according to claim 16 wherein R₅ and R₆ are the same or different and are phenyl, phenylalkyl, alkylphenyl, alkyl, or R₅ and R₆ together form alkylene a divalent chain forming a 4 to 8 membered ring structure.

18. A medical device according to claim 17 wherein R₅ and R₆ together form a divalent alkylene chain forming a 4 to 8 membered spiro, bicyclic and/or tricyclic ring structure.

19. A medical device according to claim 18 wherein R₅ and R₆ together form a 5 to 7 membered spiro, bicylic or a spiro and bicyclic ring structure.

20. A medical device according to claim 17 wherein R₅ and R₆ are the same.

21. A medical device according to claim 17 wherein R₅ and R₆ are the same or different and are alkyl, phenyl, alkylphenyl or phenylalkyl.

22. A medical device according to claim 17 wherein R₅ and R₆ are the same or different and are alkyl.

23. A medical device according to claim 22 wherein R₅ and R₆ are the same or different and are lower alkyl of from about 1 to 7 carbon atoms.

24. A medical device according to claim 23 wherein R₅ and R₆ are the same or different and are selected from the group consisting of methyl, ethyl, propyl, isopropyl, n-butyl, tertiary butyl, pentyl, neopentyl, hexyl and a secondary butyl.

25. A medical device according to claim 22 wherein R₅ and R₆ do not differ from each other by more than about 3 carbon atoms.

26. A medical device according to claim 24 wherein R₅ and R₆ do not differ from each other by more than about 2 carbon atoms.

27. A medical device according to claim 26 wherein R₅ and R₆ are alkyl of about 1 to 4 carbon atoms.

28. A medical device according to claim 27 wherein R₅ and R₆ are alkyl of about 1 to 2 carbon atoms.

29. A medical device according to claim 27 wherein R₅ and R₆ are the same and are methyl.

30. A medical device according to claim 22 wherein R₅ and R₆ are the same.

31. The fiber according to claim 3 wherein R₁, R₂, R₃ and R₄ are the same or different and are selected from the group consisting of hydrogen, alkyl, cycloalkyl, alkoxyalkyl, aryloxyalkyl, aryloxyaryl, arylalkyl and aryl and arylalkyl groups substituted with one or more alkyl, alkoxy and alkoxyalkyl groups.

32. The fiber according to claim 30 wherein R₁, R₂, R₃ and R₄ are the same or different and are selected from the groups consisting of hydrogen, alkyl, cycloalkyl, alkoxyalkyl, phenylalkyl, and phenyl substituted with one or more alkyl or alkoxy groups.

33. The fiber of claim 31 wherein:

Z is 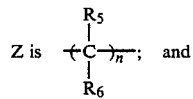; and n is 1, 2 or 3.

34. The fiber according to claim 32 wherein the homopolymer comprises a recurring moiety selected from the group consisting of:

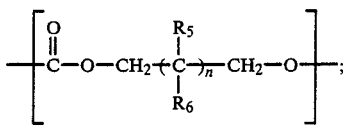

wherein:
R₅ and R₆ are the same or different and are hydrogen, alkyl, aryl, cycloalkyl, arylalkyl, alkoxyalkyl, aryloxyalkyl, or aryl or arylalkyl substituted with one or more alkyl or alkoxy groups alkoxy, alkanoyl, dialkylamino, or R₅ and R₆ together may form an alkylene chain completing a 4, 5, 6, 7, 8, 9 or 10 membered spiro, bicyclic, tricyclic ring structure or a combination thereof, which structure may optionally include one or more non-adjacent divalent carbonyl, oxa, alkylaza or arylaza groups, with the proviso that at least one of R₅ or R₆ is other than hydrogen; and n is 1, 2 or 3.

35. The fiber according to claim 3 wherein said homopolymer comprises a recurring unit of the formula:

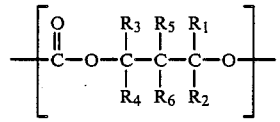

wherein:
R₁ to R₄ are the same or different and are alkyl, hydrogen, alkoxyalkyl, phenylalkyl, or phenyl substituted with one or more alkyl or alkoxy groups, wherein the aliphatic moieties include from abut 1 to about 9 carbon atoms; and R₅ and R₆ are the same or different at each occurrence and are selected from the group consisting of R₁ to R₄ substituents, aryloxy, and alkoxy, or R₅ and R₆ together form an aliphatic chain completing a 3 to 10 membered ring structure, with the proviso that at least one of R₅ or R₆ is other than hydrogen.

36. The fiber according to claim 33 wherein:
R₅ and R₆ are the same or different and are hydrogen, phenyl, phenylalkyl, phenyl substituted with one or more alkyl or alkoxy groups, or alkyl; or R₅ and R₆ together may form a divalent alkylene chain forming a 3 to 10 membered spiro, bicyclic, tricyclic ring structure or combination thereof which may optionally include one or more non-adjacent divalent carbonyl or oxa groups, with the proviso that at least one of R₅ and R₆ is other than hydrogen.

37. A fiber according to claim 35 wherein R₅ and R₆ are the same or different and are phenyl, phenylalkyl, alkylphenyl, alkyl, or R₅ and R₆ together form alkylene a divalent chain forming a 4 to 8 embered ring structure.

38. The fiber according to claim 36 wherein R₅ and R₆ are the same.

39. The fiber according to claim 37 wherein R₅ and R₆ are the same or different and are alkyl, phenyl, alkylphenyl or phenylalkyl.

40. The fiber according to claim 38 wherein R₅ and R₆ are the same or different and are alkyl.

41. The fiber according to claim 39 wherein R₅ and R₆ are the same or different and are lower alkyl of from about 1 to 7 carbon atoms.

42. The fiber according to claim 40 wherein R₅ and R₆ are alkyl of about 1 to 4 carbon atoms.

43. The fiber according to claim 41 wherein R₅ and R₆ are the same and are methyl.

44. The fiber according to claim 35 wherein R₅ and R₆ are the same.

* * * * *